United States Patent [19]

Vandervorst et al.

[11] Patent Number: 4,912,325

[45] Date of Patent: Mar. 27, 1990

[54] METHOD FOR SAMPLE ANALYSIS BY SPUTTERING WITH A PARTICLE BEAM, AND DEVICE TO IMPLEMENT SAID METHOD

[75] Inventors: Wielfried Vandervorst, Meahelen, Belgium; Bernard Rasser, Paris, France; Peter de Bisschop, Heverlee, Belgium

[73] Assignees: Cameca, Courbevoie, France; Interuniversitair Microelectronicka Centrum (IMEC), Louvain, Belgium

[21] Appl. No.: 242,134

[22] Filed: Sep. 9, 1988

[30] Foreign Application Priority Data

Sep. 11, 1987 [FR] France .................. 87 12598

[51] Int. Cl.⁴ .................. H01J 37/26; H01J 49/40
[52] U.S. Cl. .................. 250/307; 250/287; 250/309
[58] Field of Search .............. 250/281, 282, 288, 287, 250/307, 309, 423 P

[56] References Cited

U.S. PATENT DOCUMENTS

| | | | |
|---|---|---|---|
| 4,442,354 | 4/1984 | Hurst et al. | 250/281 |
| 4,611,702 | 4/1987 | Welkie | 250/309 |
| 4,694,167 | 9/1987 | Payne et al. | 250/287 |

Primary Examiner—Bruce C. Anderson
Attorney, Agent, or Firm—Oblon, Spivak, McClelland, Maier & Neustadt

[57] ABSTRACT

Disclosed are a method for the analysis of a sample by sputtering, using a particle beam, and a device to implement this method. The method consists in:

scanning the sample on a surface called a scanning surface, to hollow out a crater with a flat bed, said flat bed constituting a surface called a surface of analysis;

ionizing the particles liberated from the surface of analysis, by means of a pulsed laser beam identifying the nature of the liberated and ionized particles by means of a mass spectrometer. The idle time available between two pulses of the laser beam is used to sputter the flanks of the crater, for these flanks also have to be sputtered although they do not form part of the surface of analysis proper. Thus the time needed to sputter the sample up to a certain depth is reduced to the minimum without loss of information.

5 Claims, 4 Drawing Sheets

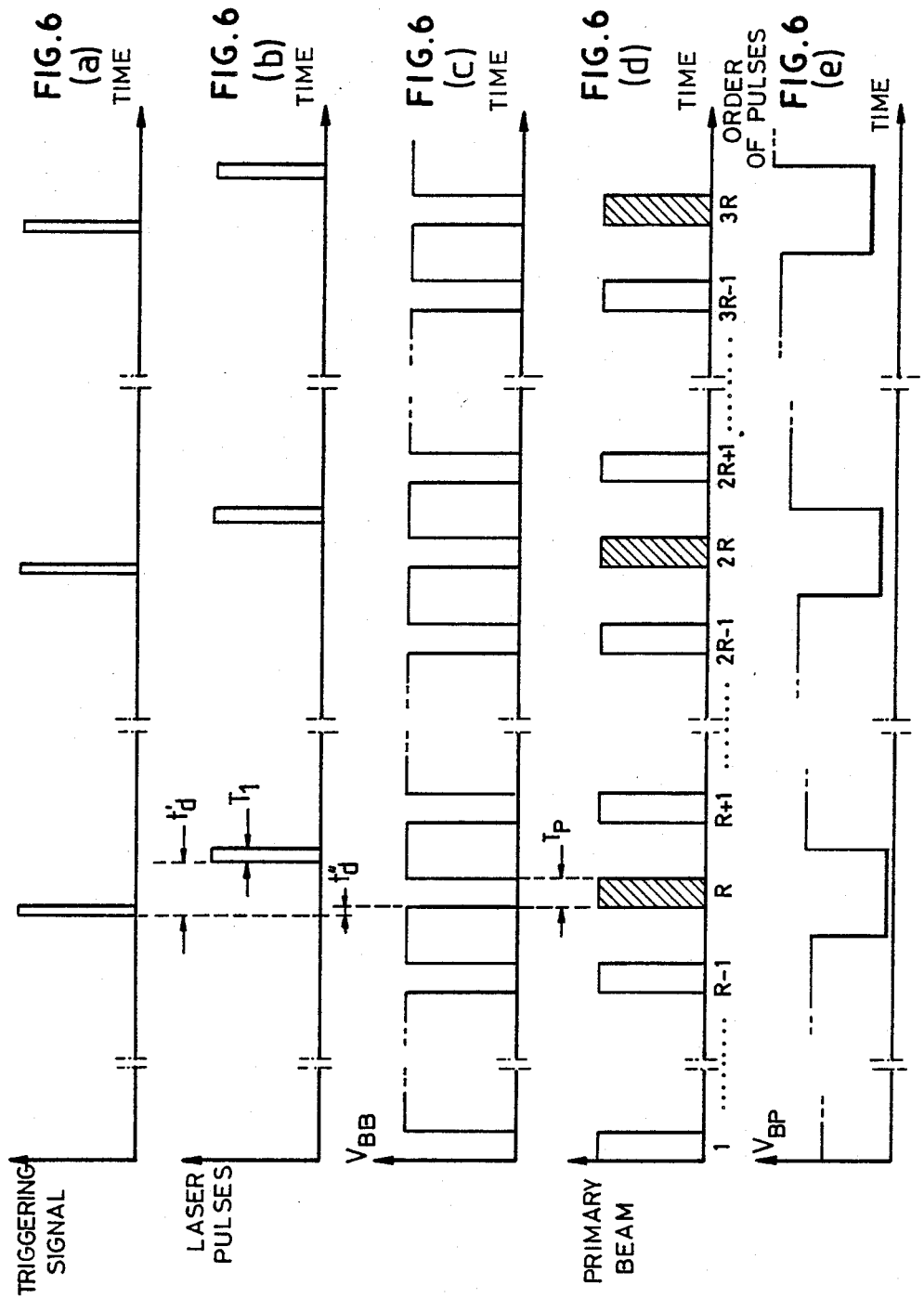

METHOD FOR SAMPLE ANALYSIS BY SPUTTERING WITH A PARTICLE BEAM, AND DEVICE TO IMPLEMENT SAID METHOD

BACKGROUND OF THE INVENTION

1. Field of the Invention

The invention concerns a method for analyzing a sample by sputtering by means of a particle beam, and to a device for the implementation of this method.

2. Description of the Prior Art

There are several known methods in the prior art for the chemical analysis of solids, using the process of sputtering by means of a particle beam. For example, in secondary ion mass spectrometry, particles are liberated from a sample to be analyzed by a beam of ions, called a primary beam, which scans the surface of the sample so as to hollow out a flat-bedded crater, and the materials liberated from the flat bed of the crater are identified by mass spectrometry.

To perform a reliable in-depth analysis of a solid sample, it is necessary to obtain a flat-bedded crater created by sputtering to form a surface to be analyzed or "surface of analysis" with a well-defined level. Generally, the primary beam is a continuous beam. For certain special applications, such as the analysis of giant molecules, a pulsed primary beam is used to enable a measurement of mass spectra by the time-of-flight technique.

More recently, new techniques have been used. These techniques consist in an additional post-ionization of the neutral particles, liberated by the primary beam, by means of a laser beam. This laser beam should be relatively high powered, and this implies the use of a pulsed laser beam. The primary beam is a beam of ions or photons produced by a continuous source, and this beam is chopped up into pulses by applying a pulsed voltage to deflection plates placed in the path of the particles between the source and the sample. The pulses of the primary beam are synchronized with the pulses of the laser in such a way that the laser pulses ionize the neutral particles liberated from the ample immediately after they have been liberated by the pulse of the primary beam.

Known methods of this type have been described, for example, in the following reference documents:
Hurst et al., Sputter Initiated Resonance Ionization Spectrometry, U.S. Pat. No. 4,442,354, Apr. 10, 1984;
J. E. Parks et al., Thin Solid Films 8 (1983) 69;
F. M. Kimock et al. Anal. Chem. 56 (1984) 2782;
M. J. Pellin et al., Surf. Science 144 (1894) 619;
C. Becker et al., Anal. Chem. 56 (1984) 1671.

Two problems are encountered in the implementing of these known methods.

A first problem concerns the time needed to make an analysis when a certain quantity of material of the sample has to be liberated, for example to make an in-depth profile measurement of the concentration of certain impurities in the sample. This is a problem because there is an incompatibility between the efficiency of an analysis and the speed with which this analysis is conducted. The post-ionization of neutral particles liberated from the sample is done by means of a pulsed laser beam because of the requirement for a relatively high-powered laser. The frequency of power laser pulses generally ranges between 10 and 200 Hz. The particles liberated by the primary beam in the interval between two consecutive pulses are clearly not all ionized and are therefore not detected. In cases where high detecting efficiency is necessary, information loss of this type is not acceptable. For this reason the primary beam is pulsed, in synchronism with the laser beam.

To obtain maximum detection efficiency, there would have to be only one pulse of the primary beam before each laser pulse. This would make the analysis very slow. For example, if the primary beam had pulses with a duration of one microsecond and a frequency of 100 Hz, its pulse ratio would be $10^{-4}$. Since the speed of analysis is directly proportionate to the sputtering speed, the speed of the analysis in this case would be smaller, by several orders of magnitude, than the speed obtained in the technique of secondary ion mass spectrometry without post-ionization, using a continuous primary beam. The measurement of a concentration profile up to a depth of one micron would take many hours. A period of time such as this is unacceptable.

To reduce the period of analysis, a known method consists in using a continuous primary beam to sputter the surface of the sample up to a certain depth, without seeking to make measurements of concentration. Then, the primary beam is chopped up into pulses which are synchronous with the pulses of the post-ionization laser beam, when the chosen depth is reached, in order to make a measurement of concentration at this depth. Then, a continuous primary beam is again used to sputter the sample until a subsequent level of depth where another measurement is made. Thus, going from level to level, this method enables an in-depth profile measurement of the concentration of impurities, while reducing the period of analysis to the minimum. However, it is clear that this measurement of the profile gives no information between each level of depth.

The aim of the invention is to propose a method of analysis by which the period of analysis can be reduced to the minimum without losing any substantial quantity of information.

A second problem relates to the making of the analyzer device, for this analyzer device should include a device for chopping the primary beam, with the following performance characteristics:

it should make it possible to obtain any pulse shape, and the pulse should be capable of being directed towards any point of the surface of the sample;

the surface of impact of the primary beam should stay the same position on the sample when the beam is on and when it is being turned off, i.e. it should not undergo any translational movements on the surface of the sample, under the effect of the voltage pulses controlling the deflection of the beam to turn it on or off;

the current of the primary beam reaching the sample should be strictly zero between the pulses of the primary beam, i.e. it should be totally off.

A second aim of the invention, therefore, is to propose an analyzer device to implement the method according to the invention while, at the same time, obtaining the above-mentioned performance characteristics

SUMMARY OF THE INVENTION

The method according to the invention consists essentially in sputtering the bed of the crater, which constitutes the surface of analysis proper, just before each laser pulse; and in sputtering the flanks of the crater, which do not constitute the surface of analysis proper but which have to be sputtered during the remaining time between two consecutive pulses, so that a crater can exist.

According to the invention, a method for the analysis of a sample by sputtering, using a pulsed particle beam called a primary beam, consists in:

deflecting the primary beam in such a way that its center scans the sample virtually, on a surface called a scanning surface, to hollow out a crater with a flat bed, said flat bed constituting a surface called a surface of analysis;

ionizing the particles liberated from the surface of analysis, by means of a pulsed laser beam synchronized with the primary beam; the frequency of the primary beam pulses being higher than the frequency of the laser beam pulses, the primary beam being deflected in such a way that its center scans a part of the scanning surface located outside the surface of analysis during a major part of the intervals between the laser beam pulses; and in such a way that it scans the surface of analysis for a period corresponding to a pulse of the primary beam just before each pulse of the laser beam;

identifying the nature of the particles, liberated from the sample and ionized, by means of a mass spectrometer.

BRIEF DESCRIPTION OF THE DRAWINGS

FIG. 6 shows timing diagrams illustrating the control signals for this exemplary embodiment.

DESCRIPTION OF A PREFERRED EMBODIMENT

Figure 1:
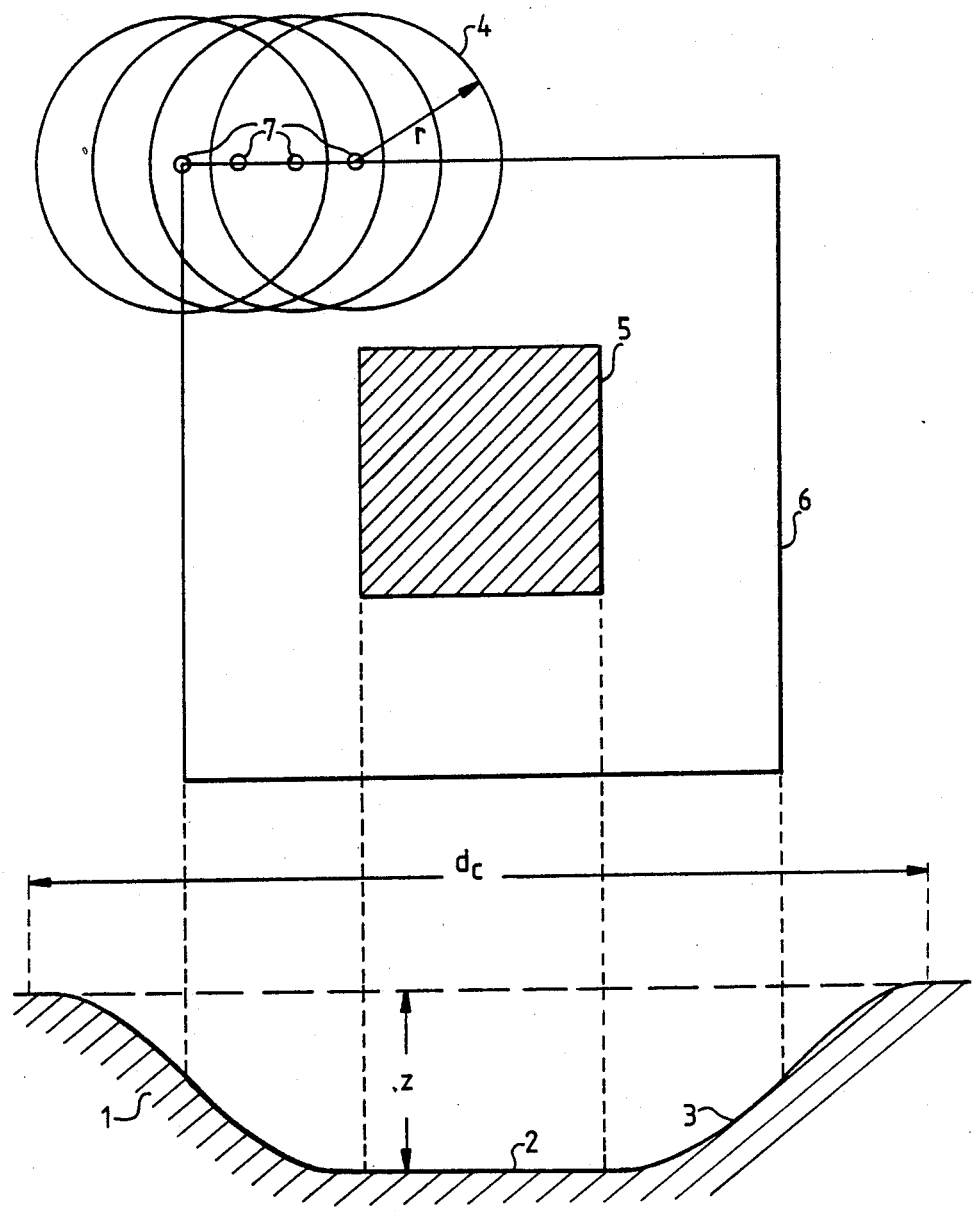
FIG. 1 gives a schematic sectional view of a crater obtained in an example of an implementation of the method according to the invention, and also shows the scanning surface and the surface of analysis corresponding to this crater.

In FIG. 1, the sample 1 undergoes a sputtering operation which hollows out a crater comprising a fat bed 2 and inclined walls 3. The surface of analysis proper consists solely of the flat bed 2 for it is located at a constant depth z. The inclined walls 3 are the inevitable result of hollowing out by sputtering, but cannot constitute a surface of analysis since they correspond to a variable depth within the sample 1. For the analysis to be reliable, the bed 2 of the crater should remain perfectly flat as and when the crater is hollowed out. For this, the walls 3 and the bed 2 should be sputtered simultaneously.

In this example of an implementation, it is assumed that the crater has an approximately square shape, as seen from above, and that the surface of impact 4 of the primary beam has a circular section with a radius r. The position of each pulse of the primary beam is identified by the position of the center 7 of its impact zone 4. The centers 7 of the impact zones of the primary beam are all located within a square zone 6 called a scanning surface. This scanning surface defines the total width $d_c$ of the crater which is sputtered in the sample. The total surface that is sputtered is hence a square with an area $d_c \times d_c$ having in distinct boundaries. This area is clearly greater than the area of the scanning surface 6. The centers 7 of the impact zones 4, which sputter the flat bed 2, are located within a square zone 5, called a surface of analysis, which has an area $S_a$ far smaller than the area $S_s$ of the scanning surface 6.

In other examples of implementation, the crater may be other than square shaped. For example, it may have a rectangular shape or a circular shape.

Figure 2:
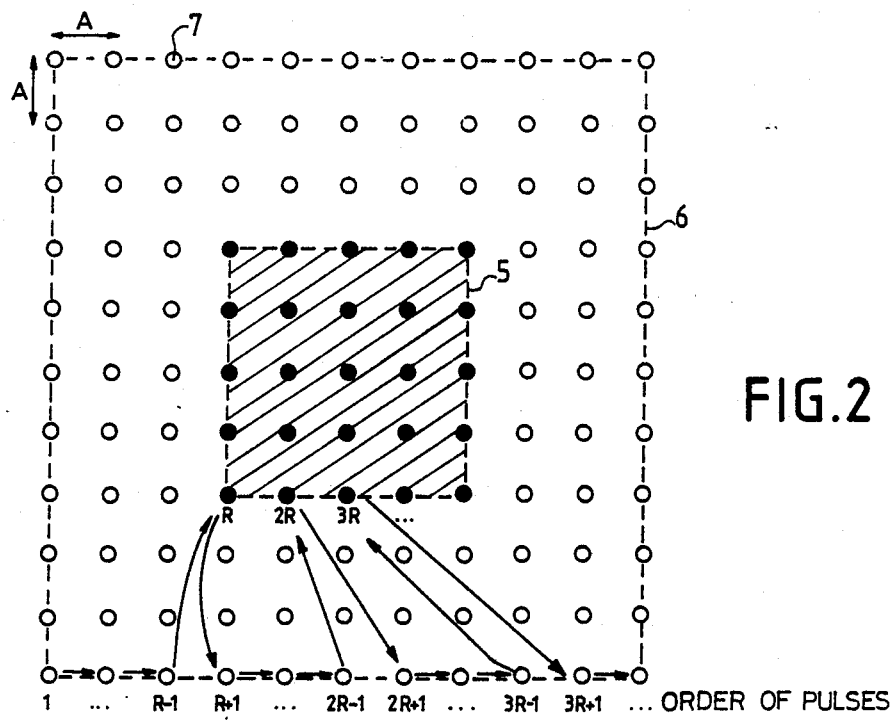
FIG. 2 shows the scan performed with the pulses of the primary beam to hollow out this crater in accordance with the method of the invention.

FIG. 2 shows the virtual scanning achieved with the primary beam, in accordance with the method according to the invention, to hollow out this crater. In this figure, blank circles represent the centers 7 of the impact zones 4 located on the surface 6 but outside the surface of analysis 5, and black circles represent the centers 7 of the impact zones 4 located within the surface of analysis 5. The zone of analysis 5 is hachured. The scanning is said to be virtual because the beam is turned off during the movements. The centers of the impact zones 4 are evenly distributed on the scanning surface 6, being separated by distances A, horizontally and vertically. The distance A is sufficiently small, compared with the radius r of each impact zone, for the overlapping of the impact zones 4 to provide homogeneous sputtering on the surface. The ratio R between the number of primary beam pulses of which the center falls within the scanning zone 6 and the total number of primary beam pulses of which the center falls within the zone of analysis 5 is equal to: $R = S_s/S_a$.

To obtain maximum information on the composition of the surface of analysis 5, no primary beam pulse should be sent to the surface of analysis so long as the laser is not ready to send a laser pulse immediately afterwards. Under these conditions, the maximum sputtering speed is obtained if the frequency of the primary beam pulses sent to the surface of analysis is exactly equal to the frequency of the laser pulses. Since the frequency of the pulses of a power laser is relatively low (a few kilohertz at the most) the interval between two consecutive laser pulses is long enough to enable the sending of additional primary beam pulses. These additional pulses are directed in such a way that the center 7 of the impact zone 4 falls in the peripheral part of the scanning surface 6, outside the surface of analysis 5. These additional pulses enable he sputtering of the walls of the crater, which is needed to subsequently deepen the flat bed of this crater.

Consequently, the primary beam pulses are sent with a constant frequency which is R times greater than the frequency of the laser pulses. The path followed by the primary beam scan is such that the center of the primary beam makes a virtual scan of the scanning surface 6, outside the surface of analysis 5, for $R-1$ pulses, then enters the zone of analysis 5 for the $R^{th}$ pulse of the primary beam, then returns outside the zone of analysis 5 for the $(R+1)^{th}$ pulse up to the $(2R-1)^{th}$ pulse, then returns to the zone of analysis 5 for the $2R^{th}$ pulse, then returns outside the zone of analysis 5 for the $(2R+1)^{th}$ pulse up to the $(3R-1)^{th}$ pulse, then goes into the zone of analysis 5 for the $3R^{th}$ pulse, then returns outside the zone of analysis 5 for the $(3R+1)^{th}$ pulse etc., until the scan of the scanning surface 6 is ended. Then the path of the scan is again travelled. The umber of steps of the scan is fixed at $256 \times 256$ for example. The user chooses the ratio R depending on the smallest concentration that he has to measure and on the maximum depth to be reached.

Figure 3:
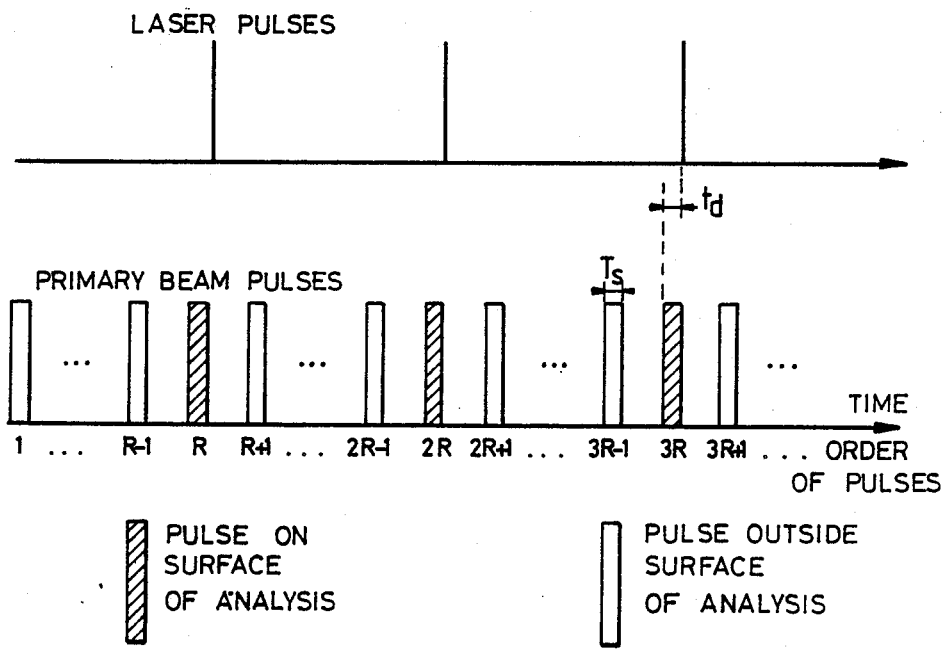
FIG. 3 shows a timing diagram of the laser pulses and the primary beam pulses in an example of an implementation of the method according to the invention.

FIG. 3 shows a timing diagram of the laser pulses and the primary beam pulses to hollow out this example of a crater. The primary beam pulses, of which the center falls on he zone of analysis 5, are hachured while the primary beam pulses, of which the center falls outside the surface of analysis 5, are blank. This timing diagram brings out the fact that a laser pulse is sent after each $R^{th}$ pulse of the primary beam, with a lag $t_d$ with respect to the start of the primary beam pulse.

It can be shown that the sputtering speed, expressed in microns per minute, is proportionate to the intensity $I_p$ of the primary beam, the duration $T_p$ of the primary beam pulses and the frequency f of the laser pulses, and that it is inversely proportionate to the area $S_a$ of the surface of analysis 5. The intensity $I_p$ and the frequency f are limited by practical considerations and the area $S_a$ has a fixed value. To increase the sputtering speed, the user may bring into play the duration $T_p$ of the primary beam pulses, but there is then an increase in the minimum measurable concentrations: in other words, the sensitivity decreases. Moreover, it is necessary to set aside a certain period of time for the movement of the primary beam since the primary beam must obligatorily be off while it is being moved, to avoid creating any uneven sputtering and to avoid distorting the measurements.

The primary beam chopping device should therefore interrupt the beam totally before it starts moving and should not turn it on again until it has reached, in a virtual way, the pre-determined position for its surface of impact. Moreover, during the period when the primary beam is on, the chopping device should not cause the slightest shift from the impact zone.

Figure 4:
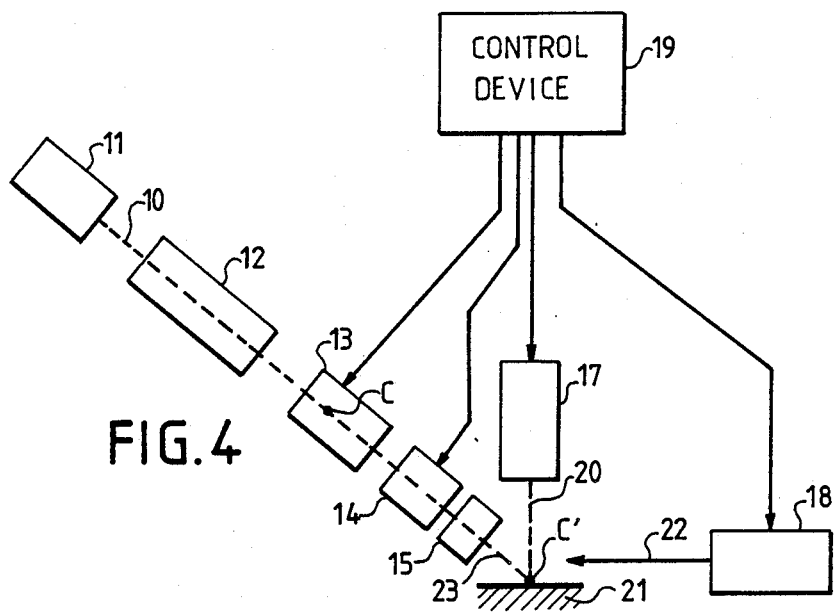
FIG. 4 gives a schematic view of an exemplary embodiment of the device according to the invention.

FIG. 4 gives a schematic view of an exemplary embodiment of the device according to the invention for the implementing of the method according to the invention. This exemplary embodiment comprises: a source of ions 11, a beam transfer device 12, a beam chopping device 13, a beam positioning device 14, a beam transfer device 15, a mass spectrometer 17, a laser 18 and a control device 19.

The primary beam 10 is formed, for example, by one of a rare gas (argon or xenon) or by other elements (gallium, indium) and its source is formed, for example, by a duo-plasmatron or by a liquid metal source giving a typical current of some micro-amperes. The ions are then accelerated to a power of some kilo-electron-volts.

The beam transfer device 12 has at least some focusing elements, but may also have a magnet, a mass selection aperture and at least one electrostatic deflector.

The device 12 should create a pupil C in the beam transfer line, at a position corresponding to the center of the beam chopping device 13. The device 13 allows the primary beam to pass towards a sample 21 only at certain well defined instants, under the control of the control device 19. The primary beam pulses leaving the device 13 are then shaped and positioned on the sample 21 by the beam transfer device 15 and by the beam positioning device 14. The device 15 may comprise, for example, one or more lenses, apertures, stigmators and deflectors. The real pupil C, produced by the beam transfer device 12, has an image C' which is formed at the surface of the sample 21.

The particles 21 of material sputtered from the sample 21 are ionized by a pulsed laser beam 22, given by the laser 18 under the control of the device 19. They are then identified by the mass spectrometer 17 which, for its part, is also controlled by the device 19.

Figure 5:
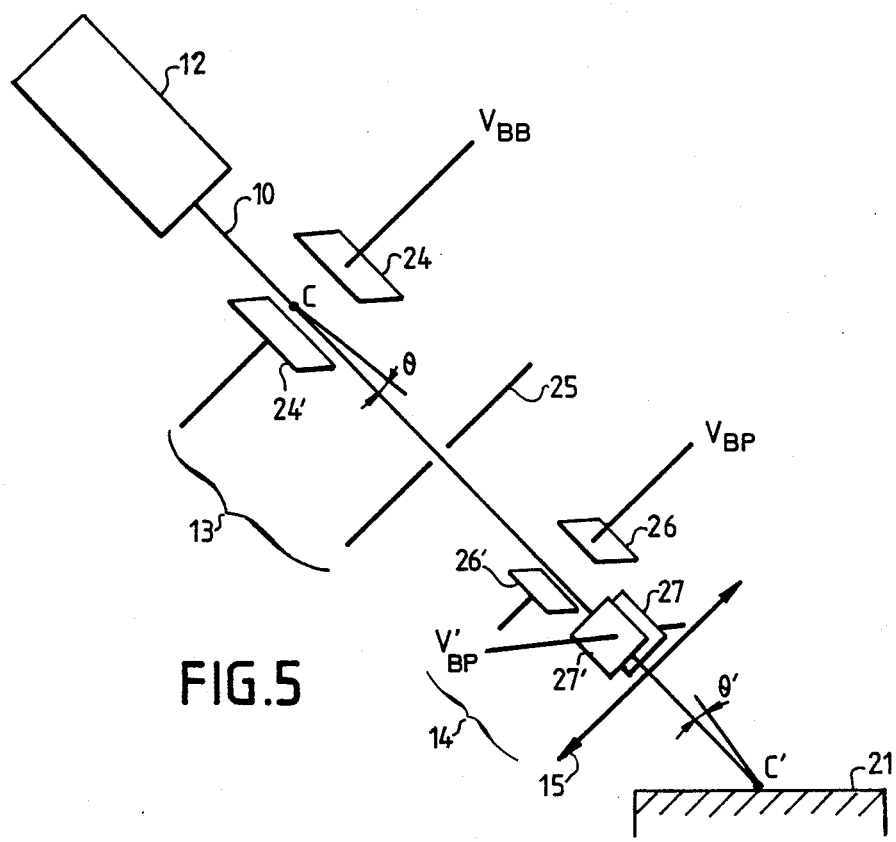
FIG. 5 gives a schematic view, in greater detail, of the exemplary embodiment shown in FIG. 3.

FIG. 5 shows a more detailed view of the device 13 for chopping the primary beam 10, the device 14 to position this beam and the beam transfer device 15, in one embodiment. The device 13 has two electrostatic deflection plates 24 and 24', placed one either side of the pupil C of the beam 10; and has a diaphragm 25 placed downline in the path of the beam 10. The plates 24 and 24' receive a potential difference $V_{BB}$ which causes an angular deflection $\theta$. This deflection causes a variation $\theta'$ in the angle of incidence of the beam 10 at the surface of the sample 21. As mentioned above, the image C' of the point C is formed on the surface of the sample 21. Consequently, this variation $\theta'$ in the angle of incidence is not accompanied by any shift in the impact zone of the beam on the surface of the sample 21. When the potential difference $V_{BB}$ is sufficient, the angle $\theta$ is sufficient for the beam 10 to be intercepted by the diaphragm 25. The beam is then turned off at the point C' without any undesirable shifting. Similarly, the beam 10 may be turned on again at the point C' without any shifting.

The beam positioning device 14 makes it possible, in the meantime, to shift the point C' where the image of the point C is formed. The device 14 has a first pair of electrostatic deflection plates, 27 and 27'. The first and second plates respectively receive the potential differences $V_{BP}$ and $V'_{BP}$ to position the beam by performing the above-described scan. The two pairs of plates have orthogonal planes of symmetry, so that they are positioned in two dimensions. The potential differences $V_{BP}$, $V'_{BP}$ and $V_{BB}$ are given by the control device 19. The device 15 is formed by a single lens in this example. In other exemplary embodiments, the device 14 may have a dual deflector with each deflector comprising two pairs of plates which are located at the same distance from the sample and are mutually orthogonal.

FIG. 6 represents timing diagrams of control signals given by the control device 19 in this exemplary embodiment. A clock signal with a frequency f triggers the laser pulses with a delay $t'_d$. In this example, the beam is transmitted by the chopping device 13 when the potential difference $V_{BB}$ is low, and it is stopped when the potential difference $V_{BB}$ is high. This voltage is periodic, with a frequency f.R. It is synchronized by the triggering signal. Each $R^{th}$ passage of $V_{BB}$ from the low level has a fixed lag $t''_d$ with respect to the triggering signal. Each passage of $V_{BB}$ to the low level turns on the primary beam for a fixed period $T_p$.

Each $R^{th}$ pulse of the primary beam is sent to the surface of analysis while the other primary beam pulses are sent outside the surface of analysis. The pulses sent to the surface of analysis are hachured in the figure while the other pulses are blank.

FIG. 6 shows a timing diagram of the potential difference $V_{BP}$. The timing diagram of the potential difference $V'_{BP}$ is not shown because it is similar. This timing diagram of $V_{BP}$ shows that, after each pulse of the primary beam, the potential difference $V_{BP}$ is modified to send the next pulse of the primary beam towards a new position. For pulses of order 1 to R−1, order R+1 to 2R−1 and order 2R+1 to 3R−1, the potential difference $V_{BP}$ has high values corresponding to a scanning zone located outside the surface of analysis 5. For the order R, 2R, 3R, . . . pulses, the potential difference $V_{BP}$ has low values corresponding to a scanning inside the surface of analysis 5.

The making of a device 19 that produces control signals of this type is within the scope of those skilled in the art. The voltages $V_{BP}$ and $V'_{BP}$ have particular shapes which can be stored in a memory, each in the form of a sequence of digital values. These values are read sequentially and converted into a potential difference by a digital/analog converter. Two different sequences of values are stored for each whole number value of the ratio R, because the user makes the value R vary according to the desired sensitivity and the maximum depth to be reached.

What is claimed is:

1. A method for the analysis of a sample by sputtering, using a pulsed particle beam called a primary beam, consisting in:

deflecting the primary beam in such a way that its center scans the sample virtually, on a surface called a scanning surface, to hollow out a crater with a flat bed, said flat bed constituting a surface called a surface of analysis;

ionizing the particles liberated from the surface of analysis, by means of a pulsed laser beam synchronized with the primary beam; the frequency of the primary beam pulses being higher than the frequency of the laser beam pulses, the primary beam being deflected in such a way that its center scans a part of the scanning surface located outside the surface of analysis during a major part of the intervals between the laser beam pulses; and in such a way that it scans the surface of analysis for a period corresponding to a pulse of the primary beam just before each pulse of the laser beam;

identifying the nature of the particles, liberated from the samples and ionized, by means of a mass spectrometer.

2. A method according to claim 1 further consisting in the producing of the primary beam pulses with a constant frequency which is R times higher than the frequency of the laser beam pulses, being a whole number greater than 1 and equal to the ratio between the area desired for the scanning surface and the area desired for the surface of analysis.

3. A method according to claim 1 wherein, in order to make a virtual scan of the sample, the primary beam is shifted virtually after it has been turned off, and it is turned on after being immobilized in its new position; and wherein, to produce the pulses of the primary beam, a continuous beam is chopped.

4. An analyzer device comprising:

means to project a pulsed particle beam, called a primary beam, on a sample to be analyzed in order to liberate particles from this sample;

means to deflect the primary beam according to a control signal;

a laser to project a pulsed laser beam to ionize particles liberated from the sample;

a mass spectrometer to identify the particles liberated from the sample and ionized;

control means to:

control the deflection means in such a way that the center of the primary beam makes a virtual scan, on the sample, of a surface called a scanning surface, to hollow out a crater with a flat bed, this flat bed constituting a surface called a surface of analysis;

control the means projecting the primary beam to send its pulses with a frequency higher than that of the laser beam pulses and in synchronism with these laser beam pulses, in such a way as to send a primary beam pulse just before each laser beam pulse;

control the deflection means in such a way that the center of the primary beam makes a virtual scan of a part of the scanning surface located outside the surface of analysis, during a major part of the time intervals between the laser beam pulses, and in such a way that it makes a virtual scan of the surface of analysis during a period corresponding to a pulse of the primary beam, just before each pulse of the laser beam.

5. A device according to claim 4 wherein the means to project a pulsed particle beam comprise:

a source giving a continuous particle beam;

a pair of electrostatic deflection plates to deflect the continuous particle beam around a pupil of this beam;

a diaphragm to intercept all the particle of the continuous beam when they re deflected beyond a fixed angle;

means to transfer a beam in order to form the image of the pupil on the sample.

* * * * *